United States Patent
Goodacre

(10) Patent No.: US 9,179,987 B2
(45) Date of Patent: Nov. 10, 2015

(54) METHOD AND DEVICE FOR REDUCING ANGULATION ERROR DURING DENTAL PROCEDURES

(71) Applicant: Loma Linda University, Loma Linda, CA (US)

(72) Inventor: Brian J. Goodacre, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 47 days.

(21) Appl. No.: 13/744,191

(22) Filed: Jan. 17, 2013

(65) Prior Publication Data

US 2013/0244196 A1    Sep. 19, 2013

Related U.S. Application Data

(60) Provisional application No. 61/610,259, filed on Mar. 13, 2012.

(51) Int. Cl.

| | |
|---|---|
| A61C 1/08 | (2006.01) |
| A61C 8/00 | (2006.01) |
| A61C 5/08 | (2006.01) |
| A61C 13/271 | (2006.01) |
| A61B 19/00 | (2006.01) |

(52) U.S. Cl.
CPC ............. *A61C 8/009* (2013.01); *A61B 19/5244* (2013.01); *A61C 1/084* (2013.01); *A61C 5/08* (2013.01); *A61C 13/26* (2013.01); *A61B 2019/5248* (2013.01)

(58) Field of Classification Search
CPC .......... A61C 8/009; A61C 5/08; A61C 1/084; A61C 13/26; A61B 19/5244; A61B 2019/5248
USPC ......... 433/27, 75, 76, 98, 103, 114, 133, 215, 433/229
See application file for complete search history.

(56) References Cited

U.S. PATENT DOCUMENTS

| | | | |
|---|---|---|---|
| 4,824,367 A | 4/1989 | Rosenstiel et al. | |
| 6,000,939 A | 12/1999 | Ray et al. | |
| 6,214,019 B1 * | 4/2001 | Manwaring et al. | 606/130 |
| 2005/0282106 A1 * | 12/2005 | Sussman et al. | 433/76 |
| 2010/0249796 A1 * | 9/2010 | Nycz | 606/99 |
| 2014/0199650 A1 * | 7/2014 | Moffson et al. | 433/27 |

* cited by examiner

*Primary Examiner* — Ralph Lewis
(74) *Attorney, Agent, or Firm* — Knobbe Martens Olson & Bear LLP

(57) ABSTRACT

A method for reducing angulation error during the placement of dental implants or other dental procedures. Two or more sensors are used to monitor realtime orientation of a dental handpiece. One or more signal emitters are used in order to notify the user that a first orientation of the dental handpiece has been identified and recorded. One or more signal emitters are used to notify the user that the dental handpiece has been repositioned into a second orientation having a predetermined spatial relationship to the first orientation.

23 Claims, 2 Drawing Sheets

METHOD AND DEVICE FOR REDUCING ANGULATION ERROR DURING DENTAL PROCEDURES

CROSS-REFERENCE TO RELATED APPLICATION

The present application claims the benefit of U.S. Provisional Patent Application No. 61/610,259, titled "Method and Device for Placing Dental Implants," filed Mar. 13, 2012, the contents of which are incorporated in this disclosure by reference in their entirety.

BACKGROUND

The placement of dental implants requires precise angulation for the best aesthetic result and longevity of the restorations that are fixed to the implants. Further, precise angulation is particularly important for proper implant functioning when occlusal forces are applied to the implant, as well as for prosthesis retention with overdentures. Additionally, improperly aligned implants can adversely affect the accuracy of impressions. Where two or more than two dental implants are implanted to support a restoration, precise angulation of the dental implants relative to each other is also required for the best function and longevity, and the least maintenance of the restoration that are fixed to implants.

Several factors can affect the alignment of implants, including anatomical variations and aesthetics, leading to sub-optimal alignment. A variety of techniques have been used to decrease angulation error during the placement of dental implants. For example, computer navigation programs have been used to produce surgical templates that guide implant placement to avoid vital structures, enhance esthetic positioning, direct placement into areas of limited bone, and permit the use of a flapless technique. These techniques increase the precision of the angular placement of dental implants, but disadvantageously, require cone beam computed tomography (CBCT) scans, and substantial training and pre-implant planning, thereby adding to the cost and time for treatment.

Therefore, there is a need for a new method for reducing angulation error during the placement of dental implants.

BRIEF SUMMARY

According to one embodiment of the present invention, there is provided a device for reducing angulation error during dental procedures, such as during the placement of dental implants. The device comprises, a) two or more than two sensors that monitor realtime orientation of the device in space; b) a programmable computer processor comprising both an input channel and an output channel connected to the two or more than two sensors; c) a computer-sensor interface for connecting to a computer for programming the device and for receiving and manipulating data from the device, the computer-sensor interface connected to the programmable computer processor; d) one or more than one signal emitter connected to the computer-sensor interface through the output channel for emitting one or more than one signal; and e) an actuator connected to the programmable computer processor by way of the input channel.

In one embodiment, the two or more than two sensors is two sensors. In another embodiment, the two or more than two sensors is three sensors. In another embodiment, the two or more than two sensors are selected from the group consisting of an accelerometer, a gyroscope and a magnetometer. In another embodiment, the two or more than two sensors are an accelerometer and a gyroscope. In another embodiment, the two or more than two sensors are an accelerometer, a gyroscope and a magnetometer.

In one embodiment, the device further comprises an integral computer connected to the computer-sensor interface for programming the device. In another embodiment, the device further comprises an integral power supply for supplying power to the device. In another embodiment, the one or more than one signal emitter is one signal emitter. In another embodiment, the one or more than one signal emitter is a plurality of signal emitters. In another embodiment, the one or more than one signal emitter is two signal emitters. In another embodiment, the one or more than one signal emitter is three signal emitters. In another embodiment, the one or more than one signal emitter emits one or more than one signal selected from the group consisting of an audible signal, a visible signal and both an audible and a visible signal. In another embodiment, at least one of the one or more than one signal emitters is integral with the device. In another embodiment, at least one of the one or more than one signal emitter is not integral with the device. In another embodiment, the actuator is integral with the device. In another embodiment, the actuator is not integral with the device.

According to another embodiment of the present invention, there is provided a system for reducing angulation error during the placement of dental implants. The system comprises, a) a device with two or more sensors that monitor realtime orientation of the device in space; a programmable computer processor comprising both an input channel and an output channel connected to the two or more sensors; a computer-sensor interface for connecting to a computer for programming the device and for receiving and manipulating data from the device, the computer-sensor interface connected to the programmable computer sensor; one or more signal emitter connecter to the computer-sensor interface through the output channel for emitting one or more signal; an actuator connected to the programmable computer processor by way of the input channel; and b) a dental handpiece connected to the device. In one embodiment, the device is integrally attached to the dental handpiece. In another embodiment, the device is reversibly attached to the dental handpiece. In a preferred embodiment, the dental handpiece is a dental drill.

According to another embodiment of the present invention, of the present invention there is provided a method for reducing angulation error during the placement of dental implants. The method comprises, a) providing a device according to the present invention; b) actuating the device to identify and record a first orientation comprising three axial planes (X, Y and Z), where the signal emitter of the device emits one or more than one signal to confirm that the device has identified and recorded the first orientation; and c) reorienting the system to a second orientation comprising three axial planes (X, Y and Z) and having a predetermined spatial relationship to the three axial planes (X, Y and Z) of the first orientation; where the one or more than one signal emitted confirming that the device has identified and recorded the first orientation is selected from the group consisting of an audible signal, a visible signal and both an audible and a visible signal. In one embodiment, the method further comprises identifying a patient with a loss of a tooth or teeth requiring one or more than one dental implant. In another embodiment, the method further comprises providing a dental handpiece, and attaching the device to the dental handpiece to create a system. In another embodiment, the device provided is part of a system comprising a dental handpiece. In one embodiment, the dental handpiece comprises a dental drill. In one embodiment, the method further comprises using the dental handpiece of the system to create a first osteotomy for a first implant in the mandible or maxilla of the patient. In another embodiment, the first orientation is recorded for an osteotomy. In another embodiment, the first orientation is recorded for a structure selected from the group consisting of an existing implant, a paralleling pin, a root socket, a template and a tooth. In another embodiment, the second orientation is the site of an implant in the mandible or maxilla of a patient. In another embodiment, the predetermined spatial relationship between one or more than one axis plane of the second orientation to the corresponding one or more than one axis plane of the first orientation is parallel. In another embodiment, the predetermined spatial relationship between one or more than one axis plane of the second orientation to the corresponding one or more than one axis plane of the first orientation is not parallel. In one embodiment, the device emits one or more than one signal to confirm that the device is at the second orientation, and the method further comprises relocating the system until the device emits one or more than one signal, thereby indicating that the device is at the second orientation, where the one or more than one signal emitted when the device is at the second orientation is selected from the group consisting of an audible signal, a visible signal and both an audible and a visible signal. In one embodiment, the device emits one or more than one signal to confirm that the device is not at the second orientation, and the method further comprises relocating the system until the device ceases to emit one or more than one signal, thereby indicating that the device is at the second orientation, where the one or more than one signal emitted when the device is not at the second orientation is selected from the group consisting of an audible signal, a visible signal and both an audible and a visible signal. In another embodiment, the method further comprises using the dental handpiece of the system to create a second osteotomy. In another embodiment, one of the sensors of the device is a magnetometer, and the method further comprises deactivating the magnetometer before identifying and recording the first orientation.

BRIEF DESCRIPTION OF THE SEVERAL VIEWS OF THE DRAWING(S)

These and other features, aspects and advantages of the present invention will become better understood with regard to the following description, appended claims, and accompanying drawings where:

DETAILED DESCRIPTION

According to one embodiment of the present invention, there is provided a device for reducing angulation error during dental procedures, such as during the placement of dental implants. In one embodiment, the device comprises two or more than two sensors that monitor realtime orientation of the device in space. According to another embodiment of the present invention, there is provided a system for reducing angulation error during dental procedures, such as during the placement of dental implants. In one embodiment, the system comprises a device according to the present invention and further comprises a dental handpiece. According to another embodiment of the present invention, there is provided a method for reducing angulation error during dental procedures, such as during the placement of dental implants. In one embodiment, the method comprises providing a device according to the present invention or providing a system according to the present invention. The device, system and method are disclosed primarily with respect to dental implants. However, as will be understood by those with skill in the art with respect to this disclosure, the device, system and method can be used for other procedures. The device, system and method will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed are not intended to be limiting nor are they intended to indicate that each step is essential to the method or that each step must occur in the order disclosed.

As used in this disclosure, the term "dental handpiece" includes a dental drill (dentist's drill) with or without a power source, as well as other dental instruments and tools useful with a device according to the present invention, as will be understood by those with skill in the art with respect to this disclosure.

As used in this disclosure, "restoration" includes a crown, a fixed complete denture, a fixed partial denture (bridge) and a removable partial denture (overdenture), as will be understood by those with skill in the art with respect to this disclosure.

Figure 1:
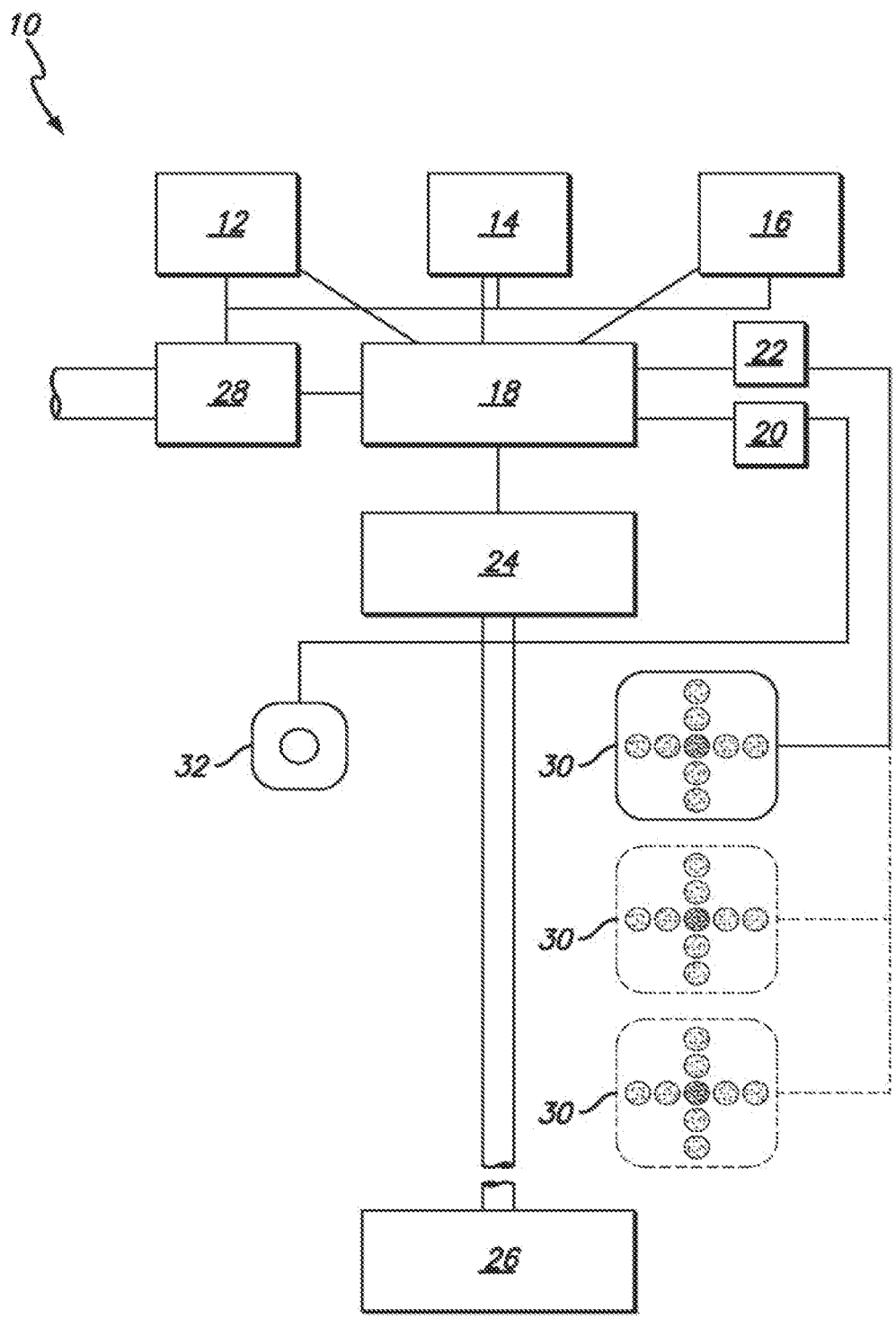
FIG. 1 is a schematic representation of a device according to the present invention.

According to one embodiment of the present invention, there is provided a device for reducing angulation error during dental procedures, such as during the placement of dental implants to receive a restoration. Referring now to FIG. 1, there is shown a schematic representation of a device according to the present invention. As can be seen, the device 10 comprises two or more than two sensors, here shown with three sensors 12, 14 and 16 as an example only. The sensors 12, 14 and 16 monitor realtime orientation of the device in space in three axial planes (X, Y and Z). In a preferred embodiment, the device comprises two sensors. In a particularly preferred embodiment, the device comprises three sensors. In one embodiment, the two or more than two sensors 12, 14 and 16 are selected from the group consisting of an accelerometer, a gyroscope and a magnetometer. In a preferred embodiment, the two or more than two sensors comprise an accelerometer and a gyroscope. In a particularly preferred embodiment as shown in FIG. 1, the device comprises three sensors, an accelerometer 12, a gyroscope 14 and a magnetometer 16. The use of a plurality of sensors allows each sensor to partially compensate for angulation error made by the other sensor or sensors, thereby decreasing total angulation error during dental procedures, such as during the placement of dental implants that would result from not using a sensor or from using a single sensor only.

In one embodiment, the device 10 further comprises a programmable computer processor 18 connected to the two or more than two sensors, and comprising both an input channel 20 and an output channel 22. In one embodiment, the device 10 further comprises a computer-sensor interface 24 connected to the programmable computer processor 18, the computer-sensor interface 24 connecting to a computer for programming the device 10 and for receiving and manipulating data from the device 10. In one embodiment, the device 10 further comprises an integral computer 26 connected to the computer-sensor interface 24 for programming the device 10, though a separate, non-integral computer can be used with an embodiment of the device 10 that lacks an integral computer 26, as will be understood by those with skill in the art with respect to this disclosure. In one embodiment, the device 10 further comprises an integral power supply 28 for supplying power to the device 10, though a separate, non-integral power supply can be used with an embodiment of the device 10 that lacks an integral power supply 28, as will be understood by those with skill in the art with respect to this disclosure.

In one embodiment, the device 10 further comprises one or more than one signal emitter 30 connected to the computer-sensor interface 18 through the output channel 22, as will be understood by those with skill in the art with respect to this disclosure. In one embodiment, the one or more than one signal emitter 30 is one signal emitter 30 (as shown in FIG. 1 in the solid lines). In a preferred embodiment, the one or more than one signal emitter 30 is a plurality of signal emitters 30. In a particularly preferred embodiment, the one or more than one signal emitter 30 is two signal emitters 30. In a particularly preferred embodiment, the one or more than one signal emitter 30 is three signal emitters 30 (as shown in FIG. 1 in the solid and broken lines). In one embodiment, the one or more than signal emitter 30 emits an audible signal (a sound). In another embodiment, the one or more than signal emitter 30 emits a visible signal (a light). In a preferred embodiment, the one or more than signal emitter 30 emits both an audible and a visible signal.

In one embodiment, one or more of the one or more than one signal emitters 30 is integral with the device 10 (directly attached to the remainder of the device 10). In one embodiment, all of the one or more than one signal emitters 30 is integral with the device 10. In another embodiment, one of the one or more than one signal emitters 30 is non-integral with the device 10 (at a significant distance, such as for example between 0.5 and 10 meters, from the remainder of the device 10). In one embodiment, all of the one or more than one signal emitters 30 is non-integral with the device 10.

In one embodiment, the device 10 further comprises an actuator 32 for operating the device 10 connected to the programmable computer processor 18 through the input channel 20, as will be understood by those with skill in the art with respect to this disclosure. In one embodiment, the actuator 32 is integral with the device 10 (directly attached to the remainder of the device 10). In another embodiment, the actuator 32 is non-integral with the device 10 (at a significant distance, such as for example between 0.5 and 10 meters, from the remainder of the device 10).

In one embodiment, the device 10 operates in one mode. In a preferred embodiment, the device 10 operates in two modes. One mode of the two modes, Axial Inclination Mode, allows a user to record the orientation in space of the device 10 in three axial planes (X, Y and Z) at a first orientation in space (the reference orientation), and then signals the user when the device 10 is oriented in a second orientation, where two of the axial planes of the second orientation are related to two of the corresponding axial planes of the first orientation by a predetermined deviation. Signaling the user can be either emitting one or more than one signal from the one or more than one signal emitters 30, or can be ceasing to emit one or more than one signal from the one or more than one signal emitters 30. For example, if the device 10 is being used to prepare the axial walls of a mandibular molar, the occlusal plane is the first orientation and the predetermined deviation for the second orientation of two of the axial planes from the first orientation is 3 degrees for the facial and lingual axial surface preparation, and 3 degrees for the mesial and distal axial surface preparation.

Another mode of the two modes, Angle Reproduction Mode, allows a user to record the orientation in space of the device 10 in three axial planes (X, Y and Z) at a first orientation in space (the reference orientation), and then signals the user when the device 10 is oriented in a second orientation, where all three axial planes of the second orientation are related to all three corresponding axial planes of the first orientation by a predetermined deviation (for example less than or equal to 0.5 degrees deviation in space).

In one embodiment, at least one of the one or more than one signal emitters 30 emits a signal when the device 10 is oriented at the second orientation and the signal would emit as long as the device 10 was oriented at the second orientation prompting the operator to maintain the second orientation of the device 10 during part or all of treatment. In another embodiment, at least one of the one or more than one signal emitters 30 ceases to emit a signal when the device 10 is oriented at the second orientation and the signal would not emit as long as the device 10 was oriented at the second orientation prompting the operator to maintain the second orientation of the device 10 during part or all of treatment;

In one embodiment, the device 10 further comprises a digital readout (such as for example two different LED number screens, or a readout on the computer 26) that allow the user to set a specific degree of rotation in two axial planes using control buttons (+/−) to establish the desired relationship between the first orientation and the second orientation.

As will be understood by those with skill in the art with respect to this disclosure, by attaching the device 10 to a dental handpiece so that the device 10 and dental handpiece move as a single unit, the user is able to maintain the dental handpiece within an orientation suitable for the dental implant, thereby reducing angulation error of the dental implant. This helps reduce the error caused by improper visualization or judgement by the surgeon.

Figure 2:
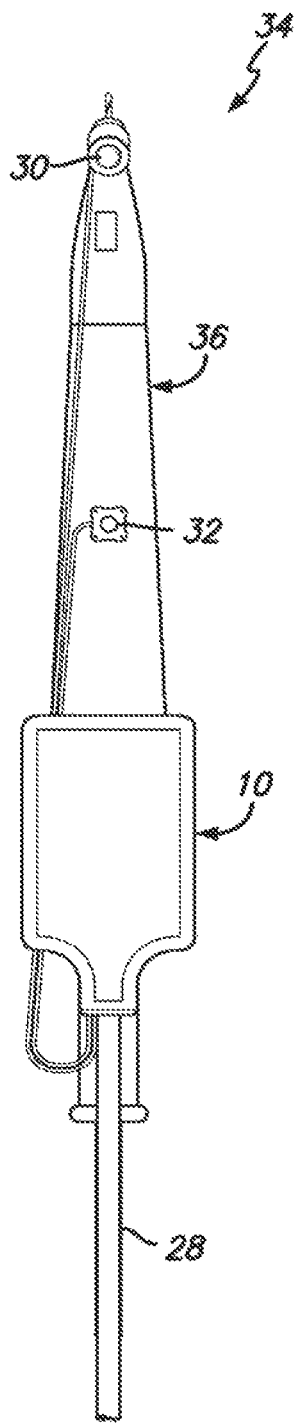
FIG. 2 is a lateral perspective view of a system according to the present invention comprising a device according to the present invention.
Figure 3:
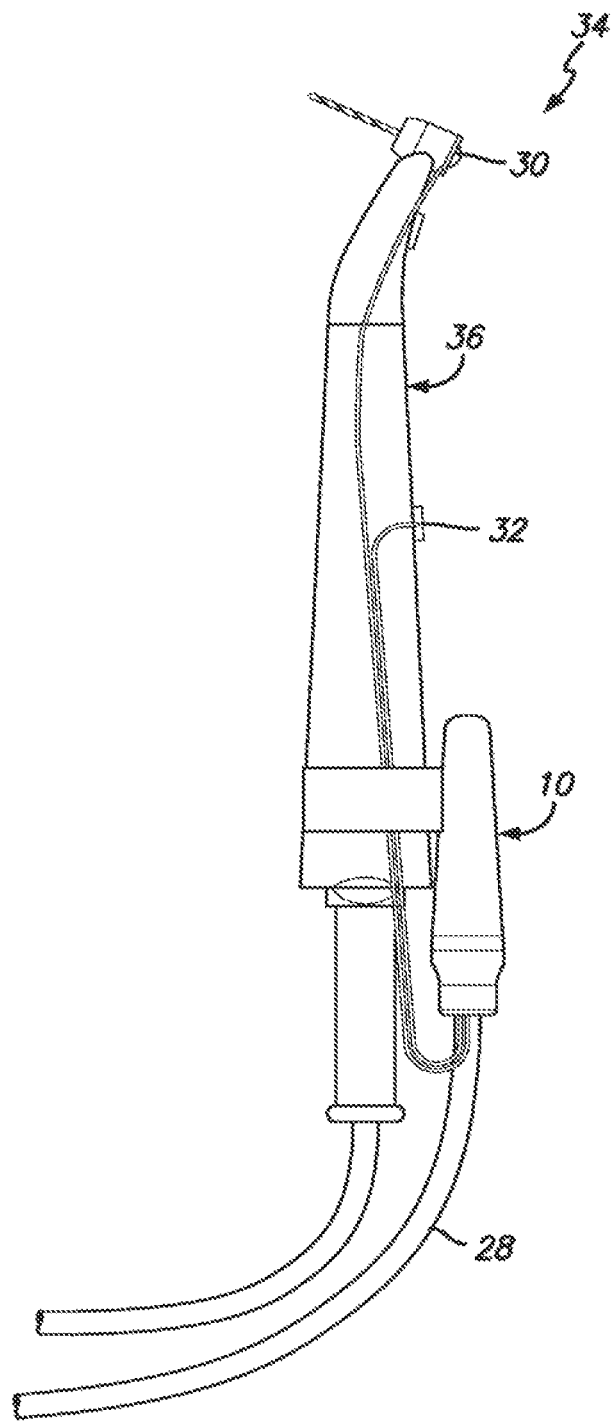
FIG. 3 is a top perspective view of the system shown in FIG. 2.

According to another embodiment of the present invention, there is provided a system for reducing angulation error during dental procedures, such as during the placement of dental implants. Referring now to FIG. 2 and FIG. 3, there are shown respectively, a lateral perspective view of a system according to the present invention comprising a device according to the present invention (FIG. 2); and a top perspective view of the system shown in FIG. 2 (FIG. 3). As can be seen, the system 34 comprises a device 10 according to the present invention and further comprises a dental handpiece 36. In a preferred embodiment, the device 10 is integrally attached to the dental handpiece 36. In a preferred embodiment, the device 10 is reversibly attached to the dental handpiece 36, such as for example by corresponding male-female type connectors.

In a preferred embodiment, both the device 10 according to the present invention, the dental handpiece 36, and the system 34 according to the present invention are sterilizable for repeat uses.

According to another embodiment of the present invention, there is provided is a method for reducing angulation error in a dental procedure. The method will now be disclosed with respect to reducing angulation error during dental procedures, such as during the placement of dental implants as an example. The method can be used with other dental procedures using corresponding steps, as will be understood by those with skill in the art with respect to this disclosure. The method comprises identifying a patient with a loss of a tooth or teeth requiring one or more than one dental implant in preparation for providing a crown, a fixed complete denture, a fixed partial denture (bridge) and a removable partial denture (overdenture) to replace the lost tooth or teeth. In a preferred embodiment, the patient is a human.

In one embodiment, the method comprises providing a device according to the present invention, and the method further comprises providing a dental handpiece, and attaching the device to the dental handpiece, thereby producing a system according to the present invention. In another embodiment, the method comprises providing a system according to the present invention.

In one embodiment, the method comprises using the dental handpiece of the system to create a first osteotomy for a first implant in the mandible or maxilla of the patient, and the method further comprises actuating the device part of the system to identify and record the orientation of the first osteotomy as a first orientation (reference orientation) while the dental handpiece is still located in the first osteotomy. In another embodiment, the method comprises using the dental handpiece of the system to identify and record a first orientation of a structure, other than a first osteotomy, as will be understood by those with skill in the art with respect to this disclosure. In one embodiment, the structure is selected from the group consisting of an existing implant, a paralleling pin, a root socket, a template (such as for example a surgical or radiographic template) and a tooth. In a preferred embodiment, the first orientation is identified and recorded with reference to three axial planes (X, Y and Z).

In one embodiment, the signal emitter of the device emits a signal to confirm that the device has identified and recorded the first orientation. In one embodiment, the signal is an audible signal (a sound). In another embodiment, the signal is a visible signal (a light, such as for example a light-emitting diode (LED)). In a preferred embodiment, the signal is both an audible and a visible signal.

Then, the method comprises reorienting the system to a second orientation comprising three axial planes (X, Y and Z) having a predetermined spatial relationship to the first orientation, such as for example to the site of an implant in the mandible or maxilla of the patient. In one embodiment, the predetermined spatial relationship between one or more than one axis plane of the second orientation to the corresponding one or more than one axis plane of the first orientation is parallel. In one embodiment, the predetermined spatial relationship between one or more than one axis plane of the second orientation to the corresponding one or more than one axis plane of the first orientation is not parallel. In one embodiment, the device emits one or more than one signal to confirm that the device is at the second orientation, and the method further comprises relocating the system until the device emits one or more than one signal, thereby indicating that the device is at the second orientation. In another embodiment, the device emits one or more than one signal to confirm that the device is not at the second orientation, and the method further comprises relocating the system until the device ceases to emit one or more than one signal, thereby indicating that the device is at the second orientation. In one embodiment, the signal is an audible signal (a sound). In another embodiment, the signal is a visible signal (a light, such as for example a light-emitting diode (LED)). In a preferred embodiment, the signal is both an audible and a visible signal. In one embodiment, one or more than one of the one or more than one signal is repeated a plurality of times during confirmation.

Then, the method comprises using the dental handpiece of the system to create a second osteotomy for a second implant in the mandible or maxilla of the patient, thereby producing the second osteotomy with the second orientation having the predetermined spacial relationship to the first orientation within a specific tolerance, and thereby reducing angulation error with respect to the first osteotomy.

As will be understood by those with skill in the art with respect to this disclosure, the method can be used to place dental implants that are parallel to each other or can be used to produce dental implants that are oriented at a predetermined spatial relationship to one another, or to another structure. In one embodiment, the method further comprises using the system to place one or more than one additional implant having a predetermined spatial relationship to the first implant or another structure, as will be understood by those with skill in the art with respect to this disclosure. In one embodiment, the method is used to place two or more than two implants. In a preferred embodiment, the method is used to place three implants. In a preferred embodiment, the method is used to place two or more than two implants that are parallel to each other.

In one embodiment, the device part of the system comprises a magnetometer, and the method further comprises deactivating the magnetometer before identifying and recording the first orientation of the first osteotomy as the reference orientation, or before actuating the device part of the system to identify a second orientation of the dental handpiece to prevent a magnetic field created by the dental handpiece from interfering with the operation of the device part of the system, as will be understood by those with skill in the art with respect to this disclosure.

EXAMPLE I

Reduction of Angulation Error Using a System According to the Present Invention

The device, system and method according to the present invention were tested as follows. The study was performed using twenty third-year dental students and five experienced clinicians (having placed more than 100 implants). Participants were numbered using a random numbering system. Students' Perceptual Ability Test (PAT) scores on the Dental Admissions Test were obtained from school administration. Fifty mandibles (Paradigm Dental Models, San Diego, Calif., US) were mounted in dental simulators (A-December, Newberg, Oreg., US). Seven marks were drawn on each of the mandibles: one for placement of a central reference pin, two on each side as locations for osteotomy placement, and one on each side for practice. To provide a standard reference osteotomy, the central osteotomy was drilled using a jig. Prior to using the system of the present invention, each participant watched an instructional video showing the procedural steps and then filled out a survey assessing their confidence before the procedure. After performing the osteotomies, participants were again surveyed regarding their post-performance confidence with and without use of the sensor and their opinion about the ease of sensor use.

For the study, each participant was evaluated on placing four osteotomies using visual alignment only (without using the system according to the present invention) with a reference pin placed in the central osteotomy, and evaluated on placing four osteotomies using a system according to the present invention but without a central reference pin (the reference osteotomy was left open). Each participant initially placed two osteotomies using a 2 mm twist drill without the system to become accustomed to the simulated mandible and the surgical handpiece. The participants then drilled four osteotomies using the 2 mm twist drill without the system in a predetermined order: site 3, site 2, site 1, and site 4 attempting to drill the four osteotomies parallel to the central reference pin.

Then, the participants drilled four osteotomies at the same location using the system according to the present invention by placing the 2 mm twist drill in the reference osteotomy and recording the first orientation. After the first orientation was set, the participants reoriented the system to the second orientation at the osteotomy site. The device was actuated such that, once the first orientation was recorded, the signal emitter emitted both a light and a sound whenever the device returned to that first recorded orientation. Therefore, as long as the light and sound were emitted, the drill on the dental handpiece was aligned in space with the reference osteotomy. The procedures were performed with the manikin in a semi-supine position to simulate patient positioning in a dental chair.

To measure alignment accuracy, carbon fiber guide pins were placed into each osteotomy and the mandibles scanned using an iCAT Cone Beam Computed Tomography machine (Imaging Science International, Hatfield, Pa., US). The files were exported and loaded into NobelClinician Software ((Nobel Biocare Services AG, Kloten, Switzerland) for angulation analysis. The angle variation was analyzed using screen shots uploaded into Google SketchUp (Google, Mountain View, Calif., US) and the results verified by placing virtual implants using NobelClinician Software to record the difference between the angulation of the reference osteotomy and each of the other osteotomies. The data was analyzed using a Related Samples Wilcoxon Signed Ranked test with the significance level being 0.05. Additionally, the participants rated their confidence level through a survey and students Perceptual Ability Test (PAT) scores were examined for correlation with osteotomy alignment.

Analyses of the results are given in Table 1.

TABLE I

Results for Twenty Third-year Dental Students and Five Experienced Clinicians

|  | Site 1 | Site 2 | Site 3 | Site 4 | Average |
| --- | --- | --- | --- | --- | --- |
| better placement with system | 36% | 32% | 40% | 28% | 34% |
| both pins within 4.1° | 12% | 32% | 36% | 16% | 24% |
| worse placement with system | 12% | 4% | 12% | 32% | 15% |
| both pins outside of 4.1° | 40% | 32% | 12% | 24% | 27% |

In addition, there were more outlying placements of the pins when the system was not used, than when the system was used. Students with higher PAT scores had rated the sensor as more difficult to use than those with lower PAT scores ($P<0.05$). There was no significant difference between students and experienced clinicians in placing the osteotomy parallel to the reference overall except for Site 1, where the experienced clinicians placed the osteotomy more parallel when not using the system than did the students when not using the system. The experienced clinicians showed a reduction in angulation error in Site 1, Site 2 ($p<0.1$) and Site 4 ($p<0.05$) in the buccal/lingual direction when using the system. Experience, PAT scores and confidence showed little to no correlation to angulation error. Using the system increased confidence level of the students but not the experienced clinicians. Experienced clinicians showed less improvement with the device then did student participants. Perceptual Ability Test scores showed an inverse relationship with reported ease of use of the system ($p<0.05$).

Therefore, as can be seen, some of the participants showed overall improvement when using the present system.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method for reducing angulation error during dental procedures, the method comprising:
   providing a device for reducing angulation error during dental procedures, the device comprising:
      two or more than two, sensors that monitor realtime orientation of the device in space;
      a programmable computer processor comprising both an input channel and an output channel connected to the two or more than two sensors;
      a computer-sensor interface for connecting to a computer for programming the device and for receiving and manipulating data from the device, the computer-sensor interface connected to the programmable computer processor;
      one or more than one signal emitter connected to the computer-sensor interface through the output channel for emitting one or more than one signal; and
      an actuator connected to the programmable computer processor by way of the input channel,
   actuating the device to identify and record a first orientation comprising three axial planes (X, Y and Z), where the one or more than one signal emitters of the device emits one or more than one signal to confirm that the device has identified and recorded the first orientation; and
   repositioning the device to a second orientation comprising three axial planes (X, Y and Z) and having a predetermined spatial relationship to the three axial planes (X, Y and Z) of the first orientation;
   where the one or more than one signal emitted confirming that the device has identified and recorded the first orientation is selected from the group consisting of an audible signal, a visible signal and both an audible and a visible signal.

2. The method of claim 1, further comprising identifying a patient with a loss of a tooth or teeth requiring one or more than one dental implant.

3. The method of claim 1, further comprising providing a dental handpiece, and attaching the device to the dental handpiece to create a system.

4. The method of claim 3, where the dental handpiece comprises a dental drill.

5. The method of claim 4, further comprising using the dental handpiece of the system to create a first osteotomy for a first implant in the mandible or maxilla of the patient without using a hole guide.

6. The method of claim 5, further comprising using the dental handpiece of the system to create a second osteotomy without using a hole guide.

7. The method of claim 1, where the device provided is part of a system comprising a dental handpiece.

8. The method of claim 7, where the dental handpiece comprises a dental drill.

9. The method of claim 8, further comprising using the dental handpiece of the system to create a first osteotomy for a first implant in the mandible or maxilla of the patient without using a hole guide.

10. The method of claim 9, further comprising using the dental handpiece of the system to create a second osteotomy without using a hole guide.

11. The method of claim 1, where the first orientation is recorded for an osteotomy.

12. The method of claim 1, where the first orientation is recorded for a structure selected from the group consisting of an existing implant, a paralleling pin, a root socket, a template and a tooth.

13. The method of claim 1, where the second orientation is a site of an implant in the mandible or maxilla of a patient.

14. The method of claim 1, where the three axial planes of the second orientation and the three axial planes of the first orientation have a predetermined spatial relationship in which one or more than one axis plane of the second orientation is parallel to the corresponding one or more than one axis plane of the first orientation.

15. The method of claim 1, where the three axial planes of the second orientation and the three axial planes of the first orientation have a predetermined spatial relationship in which each of the three axial planes of the second orientation are not parallel to the corresponding three axial planes of the first orientation.

16. The method of claim 1, where the device emits one or more than one signal to confirm that the device is at the second orientation, and the method further comprises repositioning the device until the device emits one or more than one signal, thereby indicating that the device is at the second orientation, where the one or more than one signal emitted when the device is at the second orientation is selected from the group consisting of an audible signal, a visible signal and both an audible and a visible signal.

17. The method of claim 1, where the device emits one or more than one signal to confirm that the device is not at the second orientation, and the method further comprises repositioning the device until the device ceases to emit one or more than one signal, thereby indicating that the device is at the second orientation, where the one or more than one signal emitted when the device is not at the second orientation is selected from the group consisting of an audible signal, a visible signal and both an audible and a visible signal.

18. The method of claim 1, where one of the sensors of the device is a magnetometer, and where the method further comprises deactivating the magnetometer before identifying and recording the first orientation.

19. The method of claim 1, where one of the sensors of the device is a gyroscope.

20. The method of claim 1, where two of the three axial planes of the second orientation are within a predetermined deviation of the corresponding two axial planes in the three axial planes of the first orientation.

21. The method of claim 1, where all three axial planes of the second orientation are within a predetermined deviation of their corresponding three axial planes of the first orientation.

22. The method of claim 1, where the device is capable of switching between emitting one or more than one signal to confirm that the device is at the second orientation or emitting one or more than one signal to alert that the device is not at the second orientation, where the one or more than one signal being emitted is selected from the group consisting of an audible signal, a visible signal, and both an audible and a visible signal.

23. The method of claim 1, where the device further comprises:
    a digital display that shows the predetermined spatial relationship between the first orientation and the second orientation; and
    control buttons that allow the user to set the predetermined spatial relationship between the first orientation and the second orientation.

* * * * *